United States Patent

Heacock

US010353118B2

(10) Patent No.: US 10,353,118 B2
(45) Date of Patent: Jul. 16, 2019

(54) MOLDED OPHTHALMIC LENS WITH INTEGRAL RING PORTION FOR EXAMINATION OR TREATMENT OF AN EYE

(71) Applicant: Katena Products, Inc., Denville, NJ (US)

(72) Inventor: Gregory Heacock, Maple Valley, WA (US)

(73) Assignee: Katena Products, Inc., Denville, NJ (US)

(*) Notice: Subject to any disclaimer, the term of this patent is extended or adjusted under 35 U.S.C. 154(b) by 0 days.

(21) Appl. No.: 14/482,766

(22) Filed: Sep. 10, 2014

(65) Prior Publication Data
US 2016/0070028 A1   Mar. 10, 2016

(51) Int. Cl.
*G02B 7/02*   (2006.01)
*G02B 3/04*   (2006.01)
*A61B 3/12*   (2006.01)

(52) U.S. Cl.
CPC .......... *G02B 3/04* (2013.01); *A61B 3/12* (2013.01); *G02B 7/022* (2013.01)

(58) Field of Classification Search
CPC .......... G02C 7/02; G02C 7/061; G02C 7/027; G02C 13/003; G02C 7/028; G02C 7/00; G02C 2200/00; G02B 3/04; G02B 7/022; A61B 3/12
USPC ..................................... 351/159.01
See application file for complete search history.

(56) References Cited

U.S. PATENT DOCUMENTS

| 3,589,800 A | 6/1971 | Cardona |
| 4,728,183 A | 3/1988 | Heacock et al. |
| 5,046,836 A * | 9/1991 | Volk ................ A61B 3/125 351/205 |

(Continued)

FOREIGN PATENT DOCUMENTS

| JP | H10174676 A | 6/1998 |
| WO | 2012064458 A1 | 5/2012 |

OTHER PUBLICATIONS

International Search Report and Written Opinion Report from PCT Patent Application No. PCT/US2015/44975 dated Nov. 19, 2015.

(Continued)

*Primary Examiner* — William R Alexander
*Assistant Examiner* — Henry A Duong
(74) *Attorney, Agent, or Firm* — McAndrews, Held & Malloy, Ltd.

(57) ABSTRACT

Molded ophthalmic lenses with improved optical qualities can be manufactured at high volumes at low costs to provide single-use lenses. These ophthalmic lenses are lenses for examination or treatment of the interior of an eye, are formed of an optical grade plastic, and have a ring portion integral with an optical portion. The ring portion extends from and circumferentially around the optical portion and the height of the ring portion is less than the thickness of said optical portion. These features reduce production costs and improve the optical quality of the lens including allowing any debris, bubbles and the like that tend to adhere to the surface of the mold during the molding process to collect away from the optical centerline of the lens so as to improve the optical quality of the molded ophthalmic lens and minimizing shrinkage during the molding process.

26 Claims, 2 Drawing Sheets

(56) References Cited

U.S. PATENT DOCUMENTS

| | | | |
|---|---|---|---|
| 5,319,007 A * | 6/1994 | Bright | B29D 11/00182 |
| | | | 351/159.01 |
| 5,333,017 A | 7/1994 | Volk | |
| 5,430,506 A | 7/1995 | Volk | |
| 5,523,810 A | 6/1996 | Volk | |
| 5,526,189 A * | 6/1996 | Heacock | G02B 3/04 |
| | | | 351/205 |
| 5,784,147 A * | 7/1998 | Volk | A61B 3/125 |
| | | | 351/205 |
| 6,019,472 A | 2/2000 | Koester et al. | |
| 6,120,147 A * | 9/2000 | Vijfvinkel | A61B 3/125 |
| | | | 351/159.02 |
| 6,164,779 A * | 12/2000 | Volk | A61B 3/125 |
| | | | 351/219 |
| 6,412,946 B1 * | 7/2002 | Vijfvinkel | A61B 3/125 |
| | | | 351/159.02 |
| 8,303,116 B2 | 6/2012 | Heacock | |
| 2002/0159031 A1 | 10/2002 | Kanngiesser | |
| 2003/0095234 A1 * | 5/2003 | Heacock | A61B 3/125 |
| | | | 351/219 |
| 2003/0147046 A1 | 7/2003 | Shadduck | |
| 2005/0157260 A1 * | 7/2005 | Graham | A61B 3/10 |
| | | | 351/219 |
| 2009/0244480 A1 * | 10/2009 | De Gaudemaris | G02C 7/02 |
| | | | 351/159.41 |
| 2012/0113392 A1 | 5/2012 | Heacock | |
| 2012/0242957 A1 * | 9/2012 | Mordaunt | A61B 3/125 |
| | | | 351/219 |
| 2015/0277088 A1 * | 10/2015 | Chang | G02B 13/04 |
| | | | 359/752 |
| 2015/0286068 A1 * | 10/2015 | Chene | G02B 3/08 |
| | | | 702/155 |

OTHER PUBLICATIONS

International Search Report for PCT/US2017/018068 dated May 22, 2017.
PCT/US2015/044975 International Preliminary Report, dated Mar. 23, 2017.
Supplemental Partial European Search Result, EP15839624, dated May 11, 2018.
Extended Search Report, EP 15839624.2, dated Aug. 16, 2018.
International Preliminary Report, PCT/US2017/018068, dated Aug. 30, 2018.

* cited by examiner

MOLDED OPHTHALMIC LENS WITH INTEGRAL RING PORTION FOR EXAMINATION OR TREATMENT OF AN EYE

TECHNICAL FIELD

This invention relates to a molded ophthalmic lens with improved optical qualities that can be manufactured at high volumes at low costs. For example, the invention relates to a molded ophthalmic condensing lens which provides a means for examination of the interior fundus of an eye. The invention relates to molded ophthalmic lenses which can be injection molded and/or, compression molded to provide a single use lens. The ophthalmic lens has an integral ring and aspheric shape differing from known lenses of the same type to reduce cost and improve the optical quality of the lens.

BACKGROUND

Ophthalmic lenses are used by ophthalmologists and optometrists for diagnosis and treatment of the eye. A common procedure performed by ophthalmologists is the examination of the interior of a patient's eye. This is an important procedure since variations in the appearance of the interior of a patient's eye can give an ophthalmologist important information on the health of a patient or the proliferation of a number of ocular diseases.

Commonly in an examination procedure, the ophthalmologist applies a topical drug to the patient's eye to dilate the pupil of the eye. Using a known condensing lens which the ophthalmologist holds in close proximity to the patient's eye in conjunction with an illumination system, the ophthalmologist is able to observe the interior of the patient's eye. These condensing lenses in general produce images that are useful to the ophthalmologist conducting the examination. The patient, however, must endure the various side effects of the dilation drug such as blurry vision, light hypersensitivity and poor depth perception. These side effects may persist up to several hours following an examination. Moreover, some patient's eyes do not dilate well, for example elderly patients or those taking certain medications.

U.S. Pat. No. 5,526,189, which is incorporated herein by reference, deals with a nonsymmetrical fundus observation lens or condensing lens with two aspheric surfaces which provides a means for examination of the interior of an eye and more particularly to a lens for observing a wide field of view image of the fundus of an eye through an undilated pupil.

Known ophthalmic lenses, including fundus observation lenses or condensing lenses, are generally machined and polished. Because such ophthalmic lenses are machined and polished, they are extremely costly to manufacture and cannot be produced in high volumes.

Instrument contamination and cross infection between patients is an ever present concern in the ophthalmic industry. Ophthalmic devices that must be sterilized between uses. However, this relies on personnel awareness, willingness to follow protocol, monitoring and documentation on the part of the ophthalmologist and his/her staff. Single-use devices can present a solution to this problem.

U.S. Pat. No. 8,303,116, which is incorporated herein by reference, deals with single-use, molded ophthalmic lenses that have improved optical qualities and that can be manufactured in high volumes at low costs. The lenses discussed therein have a portion that come into contact with the patient's eye and are differently-shaped than fundus observation lenses or condensing lenses.

As such, a single-use lens for use in indirect procedures, e.g. a fundus observation or condensing lens, is desirable and has not previously existed in the technical area. Additional improvements are described herein.

BRIEF SUMMARY

The disadvantages of prior ophthalmic lenses have been overcome. The present ophthalmic lenses have an optical portion with a proximal surface and an opposing surface and a ring portion extending circumferentially around the optical portion. The shape of the present lenses allows them to be used by ophthalmologists to view the interior of the patient's eye, e.g. the fundus, with or without dilation of the patient's eye. The shape of the present lenses also allows them to be formed by molding such as injection or compression molding. Since the lenses can be molded, they can be mass produced in large volume, i.e. they can be disposable or single-use.

In one embodiment, the present ophthalmic lens comprises an optical portion comprising a proximal surface and an opposing surface; and a ring portion extending circumferentially around the optical portion wherein the optical portion is formed of an optically transparent material. The lens is injection molded or compression molded which allows it to be single-use or disposable.

The ring portion can be integral with the optical portion and made of the same material as the optical portion. The axis of rotation of the ring portion can be perpendicular with the centerline of the lens.

The lens can further comprise a grip portion integral with the ring portion. As one example, the grip portion can be textured. Alternatively, the ring portion can act as a grip portion. In this alternative, the ring portion can be textured.

The lens can be formed of a material having a specific gravity of 1.1-1.2, such as 1.15-1.2. The material can have an index of refraction of 1.4 to 1.55. An example of such a material is polymethylmethacrylate.

The lens can have a thickness that is at least 10 mm, such as 10 to 20 millimeters. The lens can have a thickness ratio t/T of 0.015 to 0.2. The lens can have a diameter of at least 20 mm. The lens can have a diameter ratio d/D of 0.75 to 0.9. The lens can have a ratio of vertex curvature comparing the proximal surface to the opposing surface ranges between 1.5 and 2.0 times. The lens can have a focal length to thickness ratio F/T of 0.6-1.0. The lens can form a real image at a distance from the opposing surface of the lens that is between 5 and 40 mm.

The optical surfaces of the lens can be defined by the following formula:

$$z = Cr^2/(1+\sqrt{(1-(1+k)C^2r^2)})$$

A k value defining the surface lens can be within the range of −0.5 to −2.0.
The vertex radius (1/C) of a given surface can be within the range of 6.0 mm to 30 mm.

In another embodiment, the present ophthalmic lens comprises a main body portion comprising an optical portion and a ring portion extending circumferentially around the optical portion; and a grip portion wherein the optical portion comprises a proximal surface and an opposing surface and is formed of an optically transparent material. The lens is injection molded or compression molded which allows it to be single-use or disposable.

The ring portion can be integral with the optical portion and made of the same material as the optical portion. The axis of rotation of the ring portion can be perpendicular with the centerline of the lens. The grip portion can be textured.

The lens can be formed of a material having a specific gravity of 1.1-1.2, such as 1.15-1.2. The material can have an index of refraction of 1.4 to 1.55. An example of such a material is polymethylmethacrylate.

The lens can have a thickness that is at least 10 mm, such as 10 to 20 millimeters. The lens can have a thickness ratio t/T of 0.015 to 0.2. The lens can have a diameter of at least 20 mm. The lens can have a diameter ratio d/D of 0.75 to 0.9. The lens can have a ratio of vertex curvature comparing the proximal surface to the opposing surface ranges between 1.5 and 2.0 times. The lens can have a focal length to thickness ratio F/T of 0.6-1.0. The lens can form a real image at a distance from the opposing surface of the lens that is between 5 and 40 mm.

The optical surfaces of the lens can be defined by the following formula:

$$z = Cr^2/(1+\sqrt{1-(1+k)C^2r^2})$$

A k value defining the surface lens can be within the range of −0.5 to −2.0.

The vertex radius (1/C) of a given surface can be within the range of 6.0 mm to 30 mm.

In yet another embodiment, the present molded ophthalmic lens comprises an optical portion comprising a proximal surface and an opposing surface having a ratio of vertex curvature comparing the proximal surface to the opposing surface ranging between 1.5 and 2.0 times wherein the lens is a single-use lens. The lens is injection molded or compression molded which allows it to be single-use or disposable.

The lens can further comprise a ring portion. The ring portion can be integral with the optical portion and made of the same material as the optical portion. The axis of rotation of the ring portion can be perpendicular with the centerline of the lens.

The lens can further comprise a grip portion integral with the ring portion. As one example, the grip portion can be textured. Alternatively, the ring portion can act as a grip portion. In this alternative, the ring portion can be textured.

The lens can be formed of a material having a specific gravity of 1.1-1.2, such as 1.15-1.2. The material can have an index of refraction of 1.4 to 1.55. An example of such a material is polymethylmethacrylate.

The lens can have a thickness that is at least 10 mm, such as 10 to 20 millimeters. The lens can have a thickness ratio t/T of 0.015 to 0.2. The lens can have a diameter of at least 20 mm. The lens can have a diameter ratio d/D of 0.75 to 0.9. The lens can have a focal length to thickness ratio F/T of 0.6-1.0. The lens can form a real image at a distance from the opposing surface of the lens that is between 5 and 40 mm.

The optical surfaces of the lens can be defined by the following formula:

$$z = Cr^2/(1+\sqrt{1-(1+k)C^2r^2})$$

A k value defining the surface lens can be within the range of −0.5 to −2.0.

The vertex radius (1/C) of a given surface can be within the range of 6.0 mm to 30 mm.

These and other objects, advantages and novel features of the present invention, as well as details of an illustrative embodiment thereof, will be more fully understood from the following description and the drawing.

Figure 1:
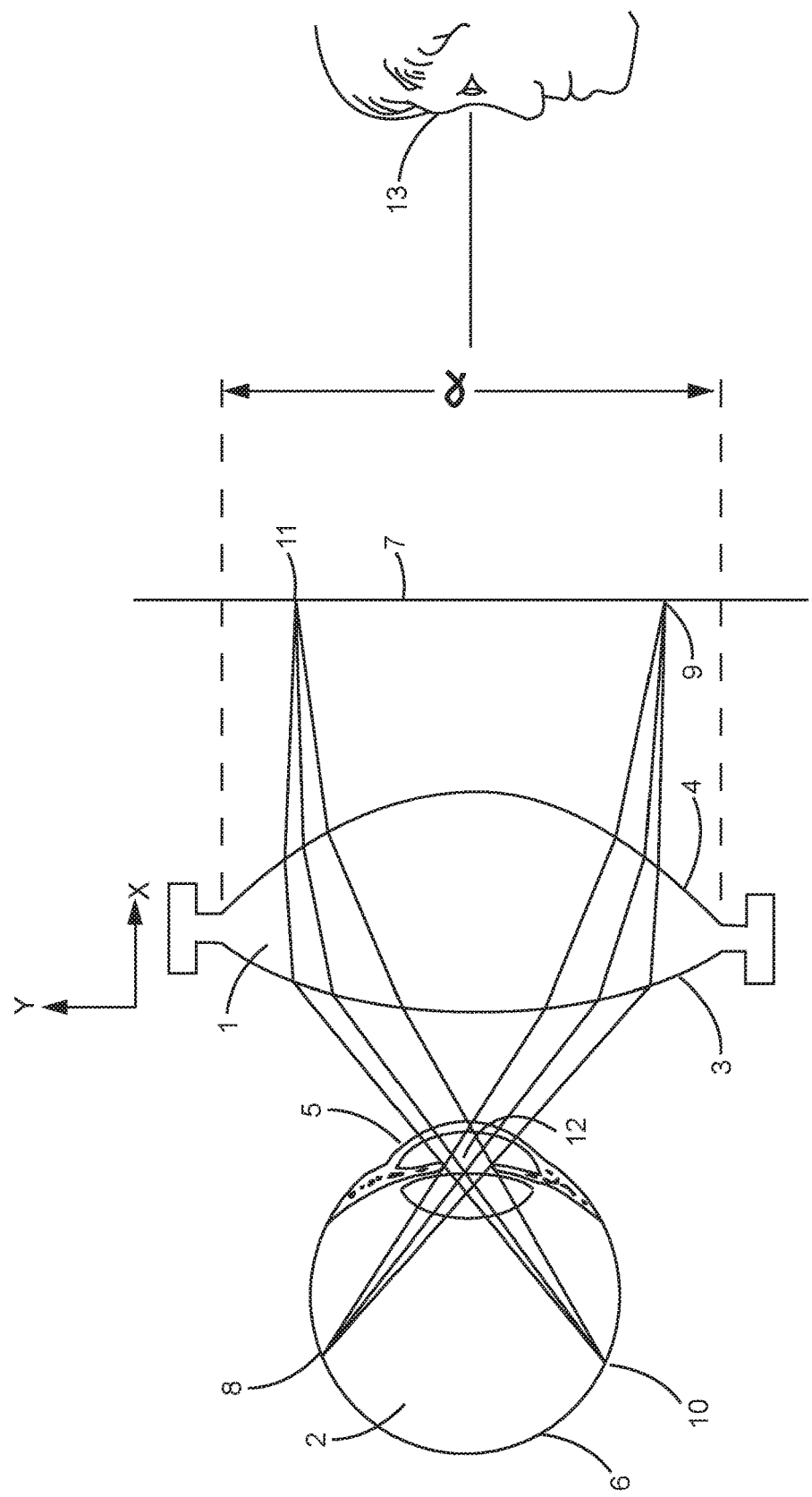
FIG. 1 is a cross-sectional schematic view of a lens of the present invention shown in close proximity to a patient's eye.

The foregoing summary, as well as the following detailed description of certain embodiments of the present invention, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION

This invention relates to a molded ophthalmic lens with improved optical qualities that can be manufactured at high volumes at low costs. For example, the invention relates to a molded ophthalmic fundus observation or condensing lens which provides for examination of the interior of an eye. The invention relates to molded ophthalmic lenses which can be injection molded and/or, compression molded to provide a single use lens. The ophthalmic lens has an integral ring and aspheric shape differing from known lenses of the same type to reduce cost and improve the optical quality of the lens.

In FIG. 1 a molded ophthalmic fundus observation or condensing lens 1 is positioned in close proximity to the patient's eye 2. The lens 1 is formed of an optically transparent material and has a first surface or proximal surface 3 that is positioned facing the patient's eye 2, adjacent to the cornea 5 and a second lens surface or opposing surface 4 that faces the observing ophthalmologist 13.

A light source, not shown, illuminates the fundus of the eye so as to produce light rays, such as the peripheral bundles of light rays 8, 10, emanating from the fundus 6 of the eye 2. The rays diverge from the fundus and pass through the pupil of the eye (dilated or undilated) 12, which is the limiting aperture of the eye. The rays exit the eye at the cornea 5 and are captured by the first surface 3 of the lens 1. The first surface 3 of the lens 1 directs the rays 8, 10 emanating from the eye 2 towards the second lens surface 4 which focuses the rays 8, 10 to respective points 9, 11 so as to form a planar, inverted real image 7 of the fundus 6. The ophthalmologist is able to observe the image 7 of the interior of the eye using, for example, an indirect ophthalmoscope, a refracting scope or even merely a pen light or the like forming the light source illuminating the eye.

The present ophthalmic lens is a molded lens. It can be injection molded and/or, compression molded. The ophthalmic lens of the present invention can be mass produced in large volumes with a high optical quality. This allows for single use lenses which can prevent contamination and disease transmission. Further, because of the single piece nature of the ophthalmic lens of the present invention and the fact that it is comprised of fewer components, the ability to produce the lens for lower cost is realized.

The ophthalmic lens is made of an optically transparent material. The optically transparent material may be any moldable material. For example, it can be a plastic material or other suitable transparent material. In one embodiment, the material is an optical grade acrylic resin such as polymethylmethacrylate (PMMA), styrene, polycarbonate or others well known in the art. The material (e.g. acrylic resin such as PMMA) can have a specific gravity of 1.1-1.9, or preferably 1.1-1.2, or preferably less than 1.19. The material can also have an index of refraction of 1.4-1.55, or preferably 1.49.

Figure 2:
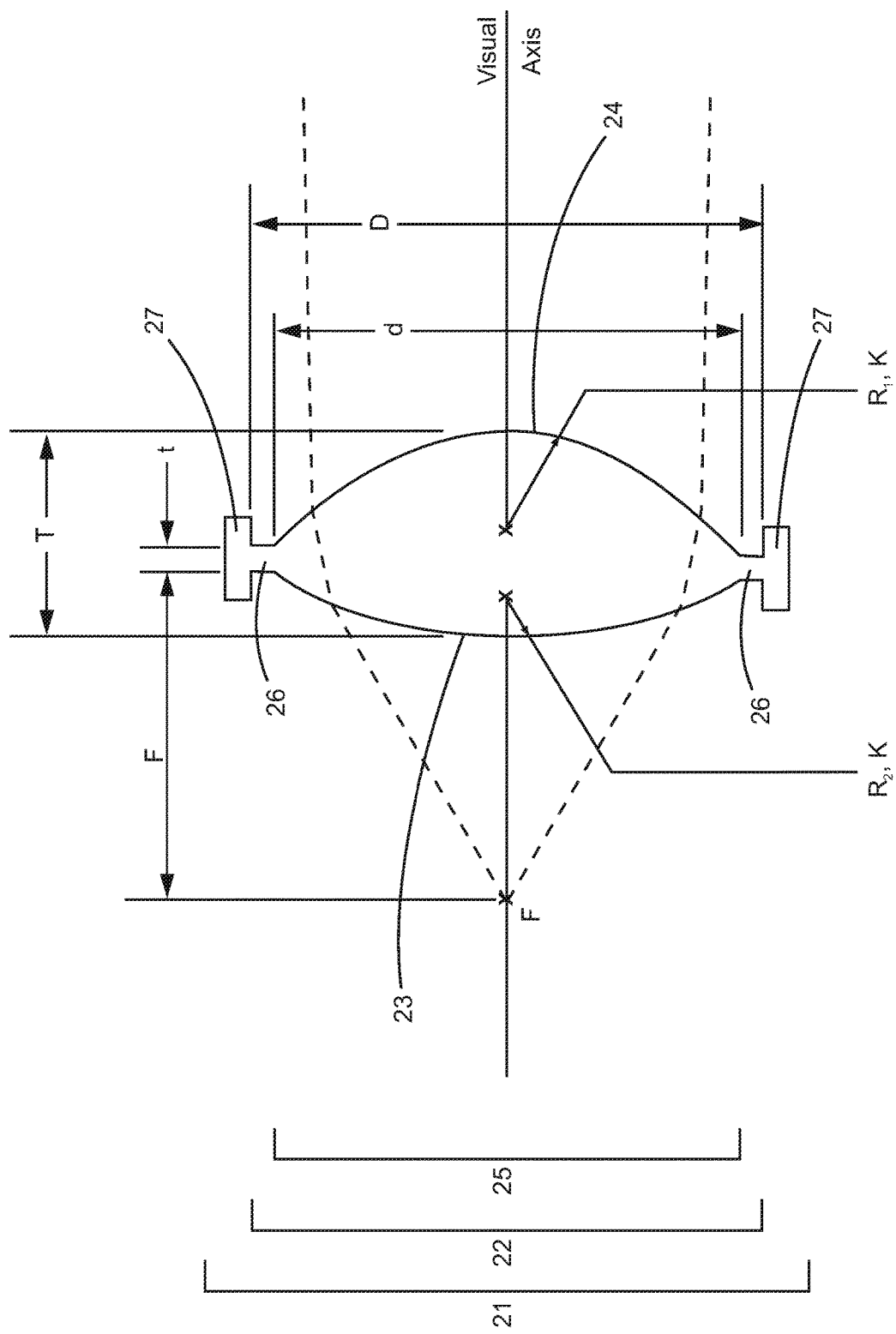
FIG. 2 is a cross-sectional schematic view of a lens of the present invention.

FIG. 2 shows an embodiment of a molded ophthalmic lens 21 according to the present application. The ophthalmic lens has a main body portion 22 which includes the optical portion 25. The optical portion is a nonsymmetric lens with two curved, nonspherical surfaces 23 and 24 specifically shaped to capture the image rays from the fundus exiting the pupil of the patient's eye to form a real inverted image of the interior of the eye having minimal distortions. The image rays from the fundus exiting the pupil of the patient's eye enter the lens at surface 23 and exit it at surface 24. The proximal surface of the main body portion 23 is proximal to the eye, but not contacting whilst the opposing surface of the main body portion 24 is away from the eye.

The optical surfaces of the lens 23 and 24 are defined by the following formula:

$$z = Cr^2/(1+\sqrt{(1-(1+K)C^2r^2)})$$

C = the curvature of the surface at the vertex of the optic
K = the conic constant, a term which flattens the curve with increase in diameter
r = is the variable relating to the optic's diameter and is increased in value from 0 (the vertex of the optical surface), to r max, (r max = ½ the diameter of the optic).
z = the geometric depth of a point on the optical surface with respect to r.

For the proximal surface 23 of the main body lens 22, having a magnification of the fundus image of the human eye of 0.67 the following values are preferred:

$$1/C = 14.0 +/- 1.0$$

$$K = -2.0 +/- 0.1$$

For the opposing surface 24 of the main body lens 22, the following values are preferred.

$$1/C = 8.0 +/- 1.0$$

$$K = -2.0 +/- 0.1$$

For an ophthalmic lens 21 having a 0.77 times magnification, the following values for the proximal surface 23 of the main body lens 22 are preferred $$1/C = 15.5 +/- 1.0$$

$$K = -2.0 +/- 0.1$$

and the following values for the opposing surface 24 of the main body lens 22 are preferred.

$$1/C = 9.6 +/- 1.0$$

$$K = -1.5 +/- 0.5$$

For an ophthalmic lens 21 having a 1.0 times magnification, the following values for the proximal surface 23 of the main body lens 22 are preferred $$1/C = 25.0 +/- 1.0$$

$$K = -1.5 +/- 0.5$$

and the following values for the opposing surface 24 of the main body lens are preferred.

$$1/C = -11.5.0 +/- 1.0$$

$$K = -1.5 +/- 0.5$$

In accordance with another embodiment of the present invention, the ophthalmic lens 21 includes two aspheric surfaces 23 and 24 each having a vertex radi, $R_1$ for the opposing surface and $R_2$ for the proximal surface. The ratio of the vertex radi of the two surfaces of curvature comparing the proximal surface 23 to the opposing surface 24 ranges between 1.5 and 2.0 times, i.e. the proximal surface is always flatter than the opposing surface. In one embodiment, the proximal lens surface 23 having a vertex radius of 14 whilst the opposing surface 24 of the main body lens has a vertex radius of 8.0 for a lens having a magnification of 0.67.

Since the surfaces of the ophthalmic lens are comprised of aspheric curves and given that the curves of the surfaces have a vertex radius where the radius of curvature most proximal to the eye is less steep than the radius of curvature of the surface opposing the eye, the lens works better than previously known lenses for viewing the fundus of patients whose eyes are difficult to dilate, e.g. elderly patients and children. Thus, clinician can also more easily view the interior of the eye for diagnosis and/or treatment.

In order to improve the ophthalmic lens 21 for molding, in one embodiment, the main body portion also has a ring portion 26. As shown in FIG. 2, the ring portion 26 is circumferentially oriented around the main body portion 22 with respect to the visual axis of the ophthalmic lens.

The height of the ring (t) related to the thickness of the lens (T) gives a thickness ratio t/T. The main body portion 22 can have a thickness ratio t/T of 0.1 to 0.2. The diameter of the optical portion (d) related to the diameter of the optical portion 25 and the ring portion (D) gives a diameter ratio d/D. The main body portion 22 can have a diameter ratio of 0.75 to 0.9. The thickness (T) can be from 10 to 20 mm. In one embodiment it is at least 10 mm.

Another important ratio is F/T or focal length over thickness. It can range from 0.6 to 1.0, preferably approximately 0.8.

The shape of the ring portion 26 integral with the optical portion and extending from the main body allows any debris, bubbles and the like that tend to adhere to the surface of the mold during the molding process to collect away from the optical centerline of the lens so as to improve the optical quality of the molded ophthalmic lens. Moreover, the shape of the ring feature also minimizes shrinkage during the molding process.

The ophthalmic lens can also have a grip portion 27 integral with the main body portion 22. In a preferred embodiment, the grip portion 27 is textured so that a clinician can easily maintain his grip on the lens 21 during diagnosis or treatment. The grip portion 27 of the ophthalmic lens 21 may have a generally cylindrical sidewall.

In one embodiment the ring portion 26 can also act as a grip portion for the clinician to easily maintain his grip on the lens 21 during diagnosis or treatment. This can be done, for example, by texturizing the ring portion 27.

The ophthalmic lenses of the present invention are shaped to optimize the molding process of the lenses and improve the optical quality of the lenses. In particular, the ophthalmic lens has an integral ring and aspheric shape differing from known lenses of the same type to reduce cost and improve the optical quality of the lens. Moreover, because the ophthalmic lenses of the present invention are molded as opposed to machined, the ophthalmic lenses of the present invention can be mass produced in volume at low cost. As such, the ophthalmic lenses of the present invention are particularly suitable for single use or disposable applications of the lenses. Because the ophthalmic lenses of the present invention are single use or disposable ophthalmic lenses that may be used once and disposed of, disease transmission via the lenses is substantially minimized.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A molded ophthalmic lens for examination or treatment of the interior of an eye comprising:
   an optical portion comprising a proximal surface and an opposing surface; and
   a ring portion integral with said optical portion and extending from and circumferentially around the optical portion
   wherein the height of said ring portion is less than the thickness of said optical portion and wherein said optical portion and integral ring portion are formed of an optical grade plastic and wherein the lens has a focal length to thickness ratio of 0.6-1.0.

2. An ophthalmic lens as recited in claim 1 wherein said lens is formed of a material having a specific gravity of 1.1-1.2 and an index of refraction of 1.4 to 1.55.

3. An ophthalmic lens as recited in claim 2 wherein said optical grade plastic is polymethylmethacrylate.

4. An ophthalmic lens as recited in claim 1 wherein said lens has a height of the ring portion to thickness of the optical portion ratio of 0.015 to 0.2.

5. An ophthalmic lens as recited in claim 4 wherein said lens has height of the ring portion to thickness of the lens ratio of 0.1 to 0.2.

6. An ophthalmic lens as recited in claim 1 wherein the lens has a diameter of the optical portion to diameter of the optical portion and ring portion ratio of 0.75 to 0.9.

7. An ophthalmic lens as recited in claim 1 further comprising a grip portion integral with the ring portion.

8. An ophthalmic lens as recited in claim 7 wherein the grip portion is textured.

9. An ophthalmic lens as recited in claim 1 wherein the optical grade plastic has a specific gravity of 1.15-1.2.

10. An ophthalmic lens as recited in claim 1 wherein an axis of rotation of the ring portion is perpendicular with the centerline of the lens.

11. An ophthalmic lens as recited in claim 1 having an index of refraction between 1.4 and 1.55.

12. An ophthalmic lens as recited in claim 1 having a thickness that is at least 10 mm.

13. An ophthalmic lens as recited in claim 1 having a diameter of at least 20 mm.

14. An ophthalmic lens as recited in claim 1 wherein the ratio of vertex curvature comparing the proximal surface to the opposing surface ranges between 1.5 and 2.0 times.

15. An ophthalmic lens as recited in claim 1 wherein the thickness of the lens ranges from 10 to 20 millimeters.

16. An ophthalmic lens as recited in claim 1 forming a real image at a distance from the opposing surface of the lens that is between 5 and 40 mm.

17. An ophthalmic lens as recited in claim 1 wherein the optical surfaces of the lens are defined by the following formula:

$$z = Cr^2/(1+\sqrt{(1-(1+k)C^2r^2)}).$$

18. An ophthalmic lens as recited in claim 1 wherein a k value defining the surface lens is within the range of −0.5 to −2.0.

19. An ophthalmic lens as recited in claim 1 wherein the vertex radius (1/C) of a given surface is within the range of 6.0 mm to 30 mm.

20. An ophthalmic lens as recited in claim 1 wherein said ring portion is textured.

21. An ophthalmic lens as recited in claim 1 wherein said lens is disposable.

22. An ophthalmic lens as recited in claim 1 wherein said optical portion is aspheric.

23. An ophthalmic lens for examination or treatment of the interior of an eye comprising:
   a main body portion comprising an optical portion integral with a ring portion extending from and circumferentially around the optical portion and wherein the height of said ring portion is less than the thickness of said optical portion; and
   a grip portion
   wherein said optical portion comprises a proximal surface and an opposing surface and the optical portion with integral ring portion are formed of an optical grade plastic and wherein the lens has a focal length to thickness ratio of 0.6-1.0.

24. An ophthalmic lens as recited in claim 23 wherein said optical portion is aspheric.

25. A molded ophthalmic lens for examination or treatment of the interior of an eye comprising an optical portion integral with a ring portion wherein the height of said ring portion is less than the thickness of said optical portion and wherein said optical portion comprises a proximal surface and an opposing surface having a ratio of vertex curvature comparing the proximal surface to the opposing surface ranging between 1.5 and 2.0 times and wherein the lens is a single-use lens and wherein the lens has a focal length to thickness ratio of 0.6-1.0.

26. An ophthalmic lens as recited in claim 25 wherein said optical portion is aspheric.

* * * * *